United States Patent [19]
Narita et al.

[11] Patent Number: 6,045,398
[45] Date of Patent: Apr. 4, 2000

[54] BATTERY ACCEPTING UNIT AND BATTERY PACK

[75] Inventors: Izuru Narita; Mitsuo Horiuchi, both of Sagamihara; Hidefumi Suzuki, Kawaski; Mitsuru Ogawa, Yamato, all of Japan

[73] Assignee: International Business Machines Corporation, Armonk, N.Y.

[21] Appl. No.: 08/945,934

[22] PCT Filed: Jul. 10, 1995

[86] PCT No.: PCT/JP95/01373

§ 371 Date: Apr. 13, 1998

§ 102(e) Date: Apr. 13, 1998

[87] PCT Pub. No.: WO97/03473

PCT Pub. Date: Jan. 30, 1997

[51] Int. Cl.[7] .................................................. H01M 2/10
[52] U.S. Cl. ............................................. 439/500; 429/96
[58] Field of Search .............................. 439/500; 429/99, 429/100, 96, 123

[56] References Cited

U.S. PATENT DOCUMENTS

| | | | |
|---|---|---|---|
| 4,731,306 | 3/1988 | Dumbser | 429/96 |
| 5,369,802 | 11/1994 | Murray | 429/96 |
| 5,863,218 | 1/1999 | Quat | 439/500 |

FOREIGN PATENT DOCUMENTS

| | | |
|---|---|---|
| 1-294351 | 11/1989 | Japan . |
| 3-138854 | 6/1991 | Japan . |
| 4-16868 | 2/1992 | Japan . |

*Primary Examiner*—Neil Abrams
*Attorney, Agent, or Firm*—Anthony N. Magistrale; A. Mitchell Harris; Andrew J. Dillon

[57] ABSTRACT

The battery accepting unit for a battery operated electric/electronic apparatus includes a plurality of positive terminals and a plurality of negative terminals. The battery accepting unit has a first position whereat a battery is connected by a pair of positive and negative terminals; a second position whereat a battery is connected by another pair of positive and negative terminals; a third position that can serve as both said first and said second positions; and a fourth position whereat a battery is connected by all positive and negative terminals. According to the battery accepting unit of the present invention, a battery pack can be exchanged without halting the power supply to an electric/electronic apparatus. Since an auxiliary power source, such as a sub-battery, is not required for an electric/electronic apparatus, a single power system, including a DC/DC converter and a charging circuit, can be provided. Therefore, the electric circuit in a system can be simplified, space can be saved inside a box, and manufacturing costs can be reduced.

11 Claims, 13 Drawing Sheets

BATTERY ACCEPTING UNIT AND BATTERY PACK

BACKGROUND OF THE INVENTION

1. Field of the Invention

The present invention relates to a battery accepting unit for a battery operated electric/electronic apparatus, such as a portable computer, and to a battery pack; and in particular to a battery accepting unit which can exchangably install a battery pack, and a battery pack. More specifically, the present invention pertains to a battery accepting unit that permits the exchange of a battery pack without halting the power supply to an electric/electronic apparatus, and to a battery pack.

2. Description of the Related Art

As a consequence of recent technical developments, for which portability and outdoor use were important considerations, compact and light electric/electronic apparatuses have become popular. So-called "notebook computers" are good examples.

In FIG. 20 is shown the outline of a notebook computer (hereinafter referred to simply as a "PC" or a "system") 100. This structure is substantially the same as a computer disclosed in Japanese Design Application No. Hei 06-30003 (Our docket No.: JA9-94-621), which was assigned to the present applicant. The PC 100 has a so-called "structure with a lid" constituted by a thin main body 110 and a lid 120 which is pivotaly hinged on the main body 110.

The lid 120 has a shallow upper case 121. A pair of cylindrical protrusions 122 are integrally formed at the lower edge of the upper case 121, and are rotatively supported by the main body 110, so as to hinge the lid 120 with the main body 110. A liquid crystal display (LCD) 123, the display means for the PC 100, is provided substantially in the center of the opened face of the upper case 121 (i.e., the reverse side of the lid 120). The lid 120 can be opened and closed relative to the main body 110 by sliding forward and backward operating portions 124 that are formed at the front on either side of the upper case 121.

The main body 110 has a shallow lower case 111. A support board 112 having a predetermined size is provided on the lower case 111 to cover the rear portion of an upper opening in the case 111. A keyboard/TrackPoint 113 ("TrackPoint" is a trademark of IBM Corp.) is provided substantially in the center of the upper opening to serve as an coordinate pointing means for the PC 100. A pair of loudspeakers 114 for audio output are provided at the right and left corners at the front of the keyboard 113. A pair of cylindrical tongue pieces 115 that are integrally formed at the rear edge of the keyboard 113 pivot at the front edge of the support board 112, hinging the keyboard 113 with the support board 112 and permitting it to be opened and closed. An indicator 117 is provided on the hinged portion at the rear end of the lower case 111. The indicator indicates the remaining capacities of a battery, the state of a PC card, the state of a floppy disk drive (FDD) and of a hard disk drive (HDD), and the status of the system 100 when the power is on.

In FIG. 21 is shown the internal structure of the main body 110 when the lid 120 and the keyboard 113 of the PC 100 are opened. A partition wall 116, which defines a front chamber and a rear chamber, is provided in the lower case 111. The partition wall 116 is formed by bending a thin metal plate into a predetermined shape. In the rear chamber, which is hidden by the support board 112 and the partition wall 116, are stored a system board (not shown), on the surface of which are mounted essential electric components, such as a CPU (Central Processing Unit), a system memory, a memory controller, a ROM, a video controller and an audio controller. This rear chamber is relatively narrow and the installation density for the electric components mounted in this chamber is very high. Into the front chamber, forward of the partition wall 116, input/output devices, such as an HDD pack 117 and a CD-ROM drive 118, and a battery pack 119 as a main power source, are detachably accommodated. Several connectors (not shown) are provided on the front side of the partition wall 116 for mechanically and electrically coupling the terminals of the HDD pack 117, the CD-ROM drive 118 and the battery pack 119.

One of the features of such a portable personal computer is that since the surface area of the box (the lower case 111) is very small, the number of openings and connectors that are provided for attachment/detachment and removal of I/O devices is limited. For example, as is shown in FIG. 20, a drawer for exchanging a CD employed as a storage medium is formed in the front of the main body 110; an exchanging opening 132 for the insertion of the battery pack 119 is formed in the right side of the main body 110; and a PC card slot 133 for inserting a PC card (two Type __/__ cards or one Type __ card) and an I/O port 134 for an external port for an external keyboard/mouse (not shown) are provided in the right side near the back of the main body 110. As is shown in FIG. 22 at the rear of the main body 110, a jack 135 for attaching a connector for an external power supply (an AC adaptor) is provided in an opening, and a serial port, a parallel port, a CRT port and a SCSI port are provided in a recessed portion and are protected by a hinged door 136. Further, as is shown in FIG. 22, in the left side of the main body 110 are formed a connector 137, for mounting an expansion adapter card that is pin-compatible with an ISA bus (Industry Standard Architecture bus; one of the input/output buses in the PC 100), and a power switch 138. In short, many devices vie for the narrow surface of the box of the PC 100. If more openings and connectors are formed, the mechanical strength of the box may be deteriorated.

Another feature of such a portable personal computer is that it is designed for a "battery operation type" using an incorporated battery, so that it can be used in places where AC power is not available. In order to supply sufficient power to the system, for the incorporated battery as a "battery pack" is used wherein a plurality of battery cells connected in series or in parallel are assembled together to form a package (e.g., the battery pack 119 in FIG. 21). Since such battery packs must be used repeatedly, rechargeable battery cells, such as those made with NiCd, NiMH or Li-Ion, are employed.

It would be easily understood that while the external AC power source is almost infinite, the capacity of a battery pack is finite. For example, a fully charged battery pack for a notebook computer supports an operating period for a PC of only two or three hours. And though this period may vary, depending on the PC model and the used conditions, the charge on the battery pack will become exhausted while the PC is in use, and the battery pack will have to be replaced by a new (or recharged) one.

Many volatile components, such as system memory and video RAM constituted by DRAM, are included among the memory devices in a PC. When the power supply is cut off, even for a moment, while the PC is in use, data currently being employed, or a file that has been completed and is being held in the volatile memory device, will be lost and will not be recoverable. As a result, a user must repeat the performance of a task from the beginning.

Such data loss will also occur when a battery pack is replaced. To cope with this problem, many battery operated electric/electronic apparatus include a relatively compact auxiliary battery (or a "sub-battery") that provides backup support only for the short period of time required to change a main battery. A portable electric/electronic apparatus that has a subsidiary power source equivalent to a sub-battery is disclosed in, for example, Japanese Examined Utility Model Publication No. Sho 63-27357, Japanese Examined Utility Model Publication No. Hei 07-4662, and Japanese Patent Application No. Hei 05-130749. In FIG. 23 is shown a conventional schematic arrangement for a power supply system in a notebook computer 100 that also employs a sub-battery.

In FIG. 23, an AC adaptor 201 converts a voltage (generally AC 100 V) input by an AC power source into a DC voltage. A battery pack 202, which is incorporated in the PC 100, consists of a plurality of battery cells, and supports a two to three hour operating period for each full charge. A circuit 203 selectively transmits the power supplied by the AC adaptor 201 and the battery pack (hereinafter also referred to as a "main battery") 202, and charges the main battery 202 using the power supplied by the AC adaptor 201. When both the AC adaptor 201 and the main battery 202 are connected to the circuit 203, the circuit 203 gives priority to the power supplied from the AC adaptor 201. A main DC/DC converter 204 reduces a DC voltage received from the AC adaptor 201, or the main battery 202, to an appropriate voltage level that the system 100 can use. A sub-battery 206 is an auxiliary for the main battery 202, and is used to back up a volatile memory in the system 100 only in a short period of time while the main battery 202 is being replaced. In response to the need to save space and to lower manufacturing costs, the sub-battery 206, as designed, is a compact power source consisting of, for example, three rechargeable NiCd or NiMH coin batteries, and has a power capacity that can support for a system 100 that is operating in a low-power consumption mode (a so-called suspend mode) for only three minutes. A circuit 207 is the charging circuit for the sub-battery 206, and a circuit 208 controls selective charging and discharging of the sub-battery 206. A sub-DC/DC converter 209 generates the voltage which can be used by the the system 100 during the discharging of the sub-battery 206, and a circuit 205 selectively supplies, to a system load 211, voltages output by the main DC/DC converter 204 and the sub-DC/DC converter 209. The system load 211 is the electric circuit in the system 100 that actually consumes power, and includes a CPU, a system memory, an HDD and a CD-ROM drive. A power management processor 210 is a specific processor for controlling the power flow from the power sources 201, 202 and 206. The power management processor 210 monitors the operating state of the system load 211, and outputs control signals to the blocks 203, 204, 207, 208 and 209. The primary controls of the power management processor 210 (1) give priority to the power supply from the AC adaptor 201 rather than from the main battery 202; (2) switch between the charging and the discharging of the main battery 202 and the sub-battery 206; (3) permit the charging of the main battery 202 and the sub-battery 206; and (4) supply power output by the main DC/DC converter 204 during normal operation, switching to the power supply output by the sub-DC/DC converter 209 only while the main battery 202 is being exchanged.

As is shown in FIG. 23, a power supply system that includes a sub-battery has already been adopted for use in, for example, the ThinkPad series ("ThinkPad" is a trademark of IBM Corp.), sold by IBM Japan, Ltd.

As is described above, a sub-battery compensates for the period during which the power supply from a main battery is cut off. However, when an electric/electronic apparatus is equipped with a sub-battery in addition to a main battery, the following problems have arisen.

(1) A power supply system other than a main power source (the AC adaptor 201 and the main battery 202) must be provided for the electric/electronic apparatus. Accordingly, an extra circuit for the sub-battery 206 is required. In the block enclosed by the broken lines in FIG. 23 are described additional components that accompany the inclusion of the sub-battery 206. These components constitute additional burdens imposed on the design of a notebook PC for which the requirements of small size, small weight and low manufacturing costs are considerations. Since the power management processor 210 has to drive the additional block, a program for this purpose is also complicated.

(2) The capacity of the sub-battery 206 is extremely small. In the previously mentioned ThinkPad series, the power is supplied by the sub-battery 206 only in the low-power consumption mode (suspend mode). During the exchange of the main battery 202, the system 100 should be switched to the low-power consumption mode (suspend mode) manually by an operator, or automatically, and is backed up by the sub-battery 206. If an operator forgets to switch to the suspend mode, or if the exchange of the main battery 202 takes more time than expected and the charge on the sub-battery 206 is exhausted, data loss occurs. And in any event, there is some possibility that data loss will occur when the parallel employment of a main battery and a sub-battery has been adopted.

Several battery exchange methods have been proposed whereby the power supply is not cut off even when a sub-battery is not used. An apparatus/system for exchanging a battery without halting the power supply is disclosed in, for example, Japanese Unexamined Patent Publications No. Sho 61-135050, No. Sho 61-250965, No. Hei 02-61959 and No. Hei 04-286860, Japanese Unexamined Utility Model Publications No. Sho 59-141652 and No. Sho 59-146861, and Japanese Examined Utility Model Publication No. Hei 04-19715.

Most of the apparatuses/systems disclosed in these publications are slide-through systems whereby a new battery is pushed in at one end of a battery storage room and an old battery is discharged from the other end. The positive and negative poles of the new and the old batteries slide along the common electrodes of the electric/electronic apparatus before the replacement is completed, so that the power supply is not halted.

In such a slide-through system, however, the insertion and extraction openings for new and old batteries must be provided in the surface of the PC. Unlike an apparatus that has extra storage space, for a notebook PC, many components vie for openings in the surface of the case, as previously described, and it is not realistic to prepare two openings for battery packs. If a new opening is formed, the mechanical strength of the case will be deteriorated. Further, room through which the new and the old battery packs are passed is required, and the sharing of a space that is larger than the footprint of the battery pack is not permitted for a case wherein the components are as crowded as is shown in FIG. 21.

Since the old battery having a low terminal voltage and a new battery having a high terminal voltage slide along the common contact pieces, this causes a short-circuit during which a large current flows from the new battery to the old battery and both batteries may be damaged. In the above described publications, however, that a short-circuit occurs between the batteries is neither pointed out nor is the issue resolved.

SUMMARY OF THE INVENTION

It is therefore one object of the present invention to provide a superior battery accepting unit and a superior battery pack, for a battery operated electric/electronic apparatus, such as a portable computer.

It is another object of the present invention to provide a battery accepting unit for which a battery pack can be efficiently exchanged, and a battery pack.

It is an additional object of the present invention to provide a battery accepting unit that permits a battery pack to be exchanged without the power to an electric/electronic apparatus being shut down, even for a moment.

It is a further object of the present invention to provide a battery accepting unit for which a battery pack can be exchanged even without a sub-battery being used and without the power to an electric/electronic apparatus being shut down, and a battery pack.

To achieve the above objects, according to a first aspect of the present invention, a battery accepting unit, for a battery operated electric/electronic apparatus, has: a plurality of positive terminals; and a plurality of negative terminals.

According to a second aspect of the present invention, a battery accepting unit, for a battery operated electric/electronic apparatus, which includes a plurality of positive terminals and a plurality of negative terminals, and which has a first position where a battery is connected by a pair of positive and negative terminals; a second position where a battery is connected by another pair of positive and negative terminals; a third position that can serve as both the first and the second positions; and a fourth position where a battery is connected by all positive and negative terminals.

Preferably, a battery accepting unit according to the second aspect should have a locking mechanism for inhibiting a removal of the battery in the first position. The locking mechanism may permit removal of the battery in the fourth position.

According to a third aspect of the present invention, provided is a battery accepting unit, for a battery operated electric/electronic apparatus, has: a shallow bottom; a plurality of positive terminals provided on a first side wall of the unit; and a plurality of negative terminals provided on a second side wall opposite the first side wall.

According to a fourth aspect of the present invention, provided is a battery accepting unit, for a battery operated electric/electronic apparatus, has: a shallow bottom; a plurality of positive terminals provided on a first side wall of the unit; and a plurality of negative terminals provided on a second side wall opposite said first side wall, a pair of positive and negative terminals being able to be connected to a battery while another pair of positive and negative terminals are connected to another battery.

Preferably, a battery accepting unit according to the fourth aspect has a locking mechanism for inhibiting a removal of the battery when the battery accepting unit is connected to only one battery by one pair of positive and negative terminals.

The battery accepting unit may include detection means for detecting the connection of another battery by another pair of positive and negative pairs, and unlocking means for unlocking the locking mechanism in accordance with a result of a detection obtained by the detection means.

According to a fifth aspect, provided is a battery accepting unit, for a battery operated electric/electronic apparatus, includes: three first electrode terminals connected in parallel; two electrode terminals connected in parallel and having polarities opposite those of the first electrode terminals; and a backflow prevention device inserted into two of the first electrode terminals.

According to a sixth aspect of the present invention, a battery pack, for a battery operated electric/electronic apparatus, has: a plurality of positive terminals; and a plurality of negative terminals.

According to a seventh aspect of the present invention, a plane and substantially flat battery pack, for a battery operated electric/electronic apparatus, has: semicircular side portions; a first end face having three positive terminals; and a second end face opposite the first end face that includes two negative terminals.

According to the battery accepting unit and the battery pack of the present invention, a battery pack can be changed without the power to the electric/electronic apparatus being shut down.

Since an auxiliary power source, such as a sub-battery, is not required, only a single power system, to include the DC/DC converter and a charging circuit, must be provided. Therefore, the electric circuit in the system is simplified, and room in the interior of the case of the apparatus can be saved and manufacturing costs can be reduced.

The other objects, features, and advantages of the present invention will become apparent in due course during the detailed description of the embodiment of the present invention, which will be given while referring to the accompanying drawings.

DESCRIPTION OF THE ILLUSTRATIVE EMBODIMENTS

Figure 1:
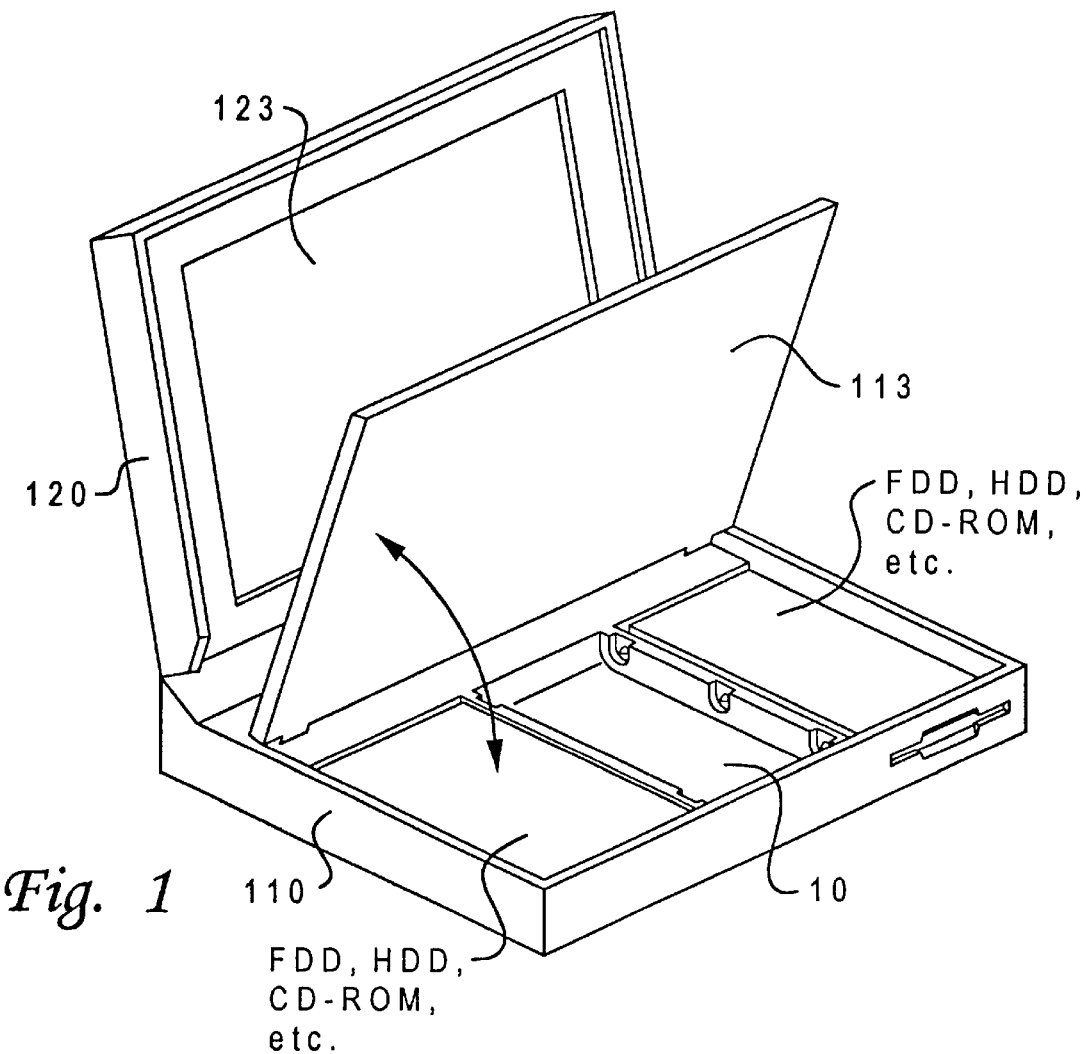
FIG. 1 is a diagram illustrating the outline of a notebook PC 100 according to a first embodiment of the present invention.

The preferred embodiments of the present invention will now be described in detail while referring to the drawings. Within the drawings, the references associated with various elements are described in the table below, as well as in the description to follow.

| | |
|---|---|
| 10. | Battery compartment |
| 20. | Battery pack |
| 100. | Personal computer |
| 110. | Personal computer |
| 111. | Lower casing |
| 112. | Supporting plate |
| 113. | Keyboard/track point |
| 114. | Speaker |
| 115. | Flap |
| 115A. | Indicator unit |
| 116. | Spacer |
| 117. | HDD pack |
| 118. | CD ROM drive |
| 119. | Battery pack |
| 120. | Cover |
| 121. | Upper casing |
| 122. | Protrusion |
| 123. | LCD |
| 124. | Opening/closing operation member |
| 201. | AC adaptor |
| 202. | Main battery (battery pack) |
| 203. | AC/DC switching circuit/main battery charging circuit |
| 204. | Main DC/DC converter |
| 205. | Main/auxiliary power source switching circuit |
| 206. | Auxiliary battery |
| 207. | Auxiliary battery charging circuit |
| 208. | Power switching circuit for charging or discharging |
| 209. | Auxiliary DC/DC converter |
| 210. | Power control processor |
| 211. | System load |

A. First Embodiment

The structures of a PC 100, a battery accepting unit 10 and a battery pack 20 according to a first embodiment of the present invention will now be explained while referring to FIGS. 1 through 7. The same reference numerals as are used in FIGS. 20 through 23 are also used to denote corresponding or identical components.

In FIG. 1 is shown the appearance of the notebook PC 100 according to the embodiments of the present invention. The PC 100 is a structure having a lid, which is the same as that described in "4. Description of the Background" and in FIGS. 20 and 21. A lid 120 and a keyboard 113 can be opened relative to a main body 110. The front room in the main body 110 that is hidden by the keyboard 113 is used to accommodate removable devices, such as an HDD pack, an FDD pack and a CD-ROM drive, and a battery pack (main battery) 20. In this case, the center portion of the front room is used as a battery pack accepting unit 10.

Figure 2:
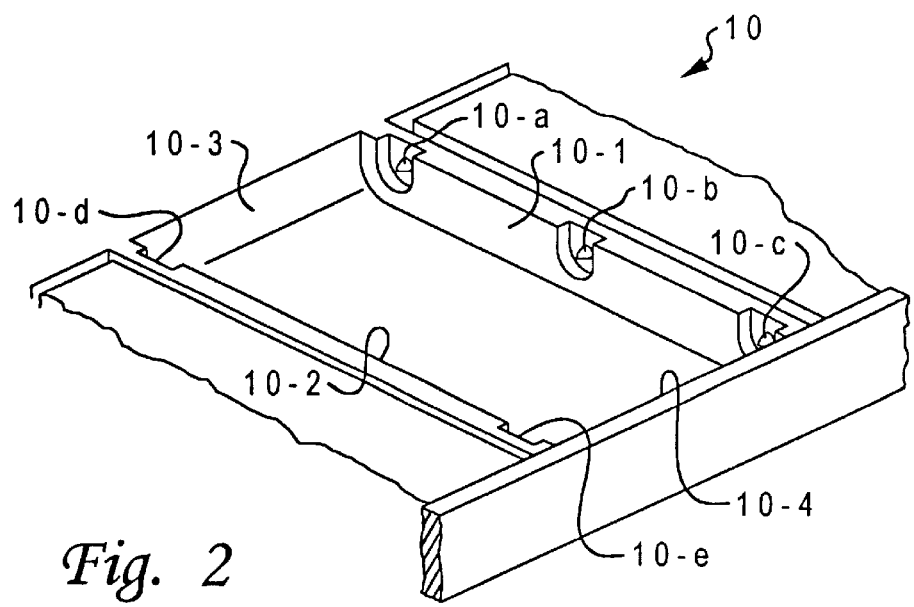
FIG. 2 is an enlarged perspective view of a battery accepting unit 10.

FIG. 2 is an enlarged perspective view of the battery accepting unit 10.

The battery accepting unit 10 is defined by a right wall 10-1, a left wall 10-2, a rear wall 10-3 and a front wall 10-4. The battery accepting unit 10 and the battery pack 20 in this embodiment have a multi-terminal structure, each having a plurality of both positive and negative terminals (three positive terminals and two negative terminals). The right wall 10-1 is a face for contacting the positive pole of the battery pack 20, and includes three terminals 10-a, 10-b and 10-c. The left wall 10-2 is a face for contacting the negative pole of the battery pack 20, and includes two terminals 10-d and 10-e. Tongue-shaped recessed portions are formed at the terminals 10-a through 10-e, and terminals (contact elements), which will be described later (see FIGS. 4 and 5), are mounted in the center of the recessed portions. The bottom edges of the front and rear walls 10-3 and 10-4 are curved, bow shaped, and are fitted to the curved side faces of the battery pack 20, which will be described later.

Figure 3:
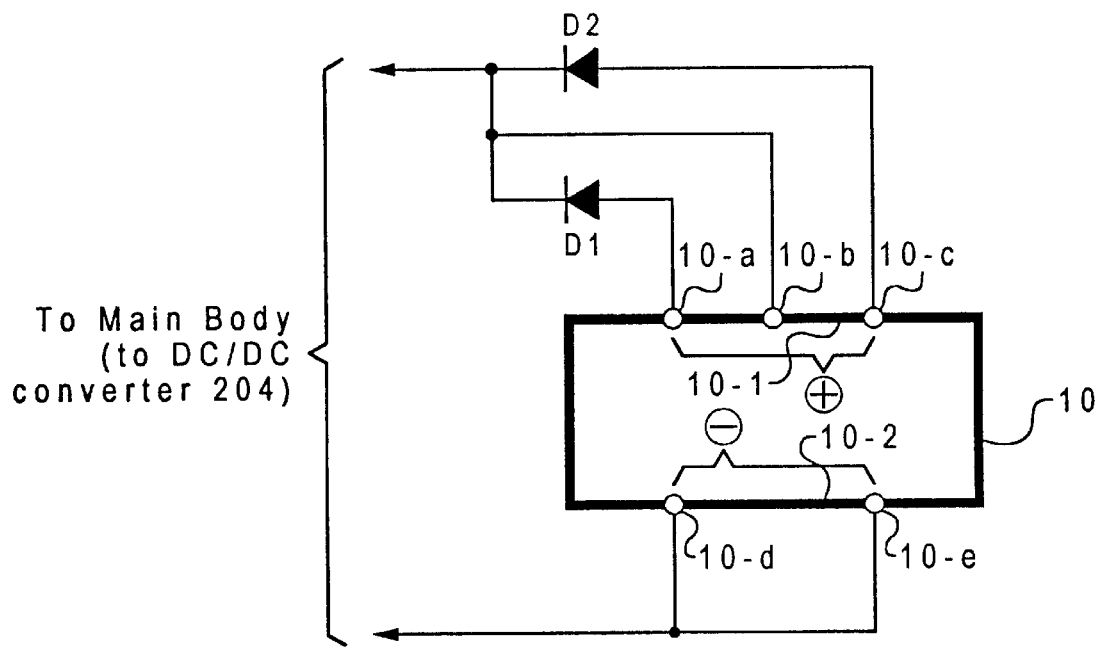
FIG. 3 is an electric circuit diagram for the battery accepting unit 10.

In FIG. 3 is shown an electric circuit in the battery accepting unit 10. The three positive terminals 10-a, 10-b and 10-c and the two negative terminals 10-d and 10-e are collected to one power line respectively, which runs forward to the DC/DC converter 204 in the PC 100. Backflow prevention diodes D1 and D2 are connected to the positive terminals 10-a and 10-c in the forward direction of the battery discharge. When the battery pack 20 has been loaded and contact has been made with all the positive terminals 10-a, 10-b and 10-c, because of the internal resistance provided by the diodes D1 and D2 (which will be described later), a current flows only from the terminal 10-b. Since the diodes D1 and D2 are so connected to each other between the terminals 10-a and 10-c, while the cathodes face each other, no current flows between the terminals 10-a and 10-c. The diodes D1 and D2 can prevent a short-circuit during the exchange of new and old batteries. This will later become apparent later from the explanation.

Figure 4:
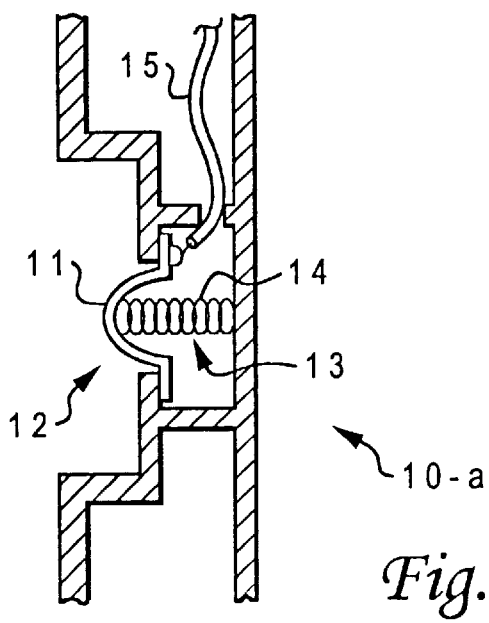
FIG. 4 is a horizontal cross-sectional view of a terminal portion in the battery accepting unit 10.
Figure 5:
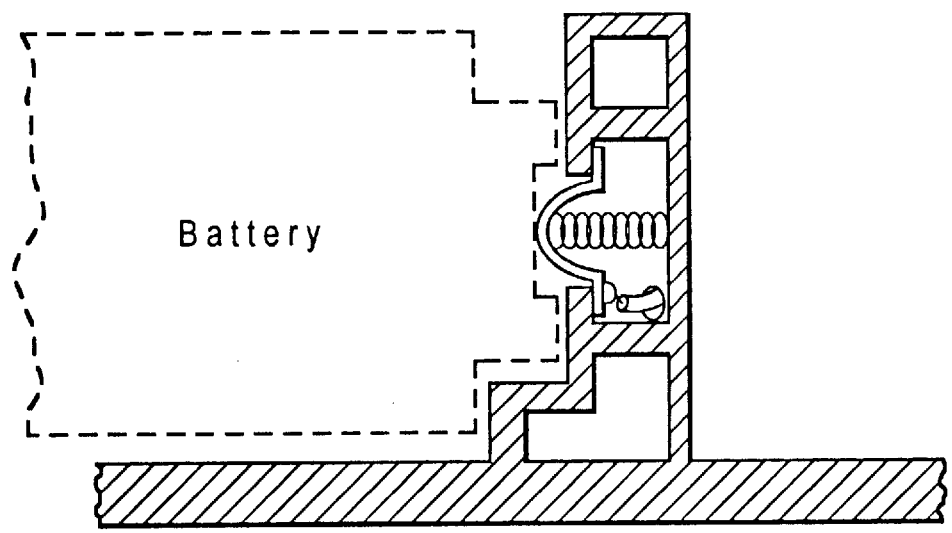
FIG. 5 is a vertical cross-sectional view of the terminal portion in the battery accepting unit 10.

FIGS. 4 and 5 are a horizontal cross-sectional view and a vertical cross-sectional view of the terminal 10-a of the battery accepting unit 10. It should be understood that the other terminals 10-b through 10-e have almost the same structure.

The center of the tongue-shaped recessed portion is an opening 12 through which protrudes a terminal (contact element) 11. At the rear of the opening 12, a chamber 13 is formed in which is mounted the contact element. The contact element 11 is a conductive part with a protrusion at its center, and is formed by applying pressure to a thin, elastic metal piece, for example. A spring 14 is provided at the rear face of the protrusion of the contact element 11. The contact element 11 is driven forward by the restoring force of the spring 14, and projects outward through the opening 12. A lead line 15 is soldered to one end of the contact element 11 in order to communicate electrically with a predetermined electric circuit (the DC/DC converter 204).

Figure 6:
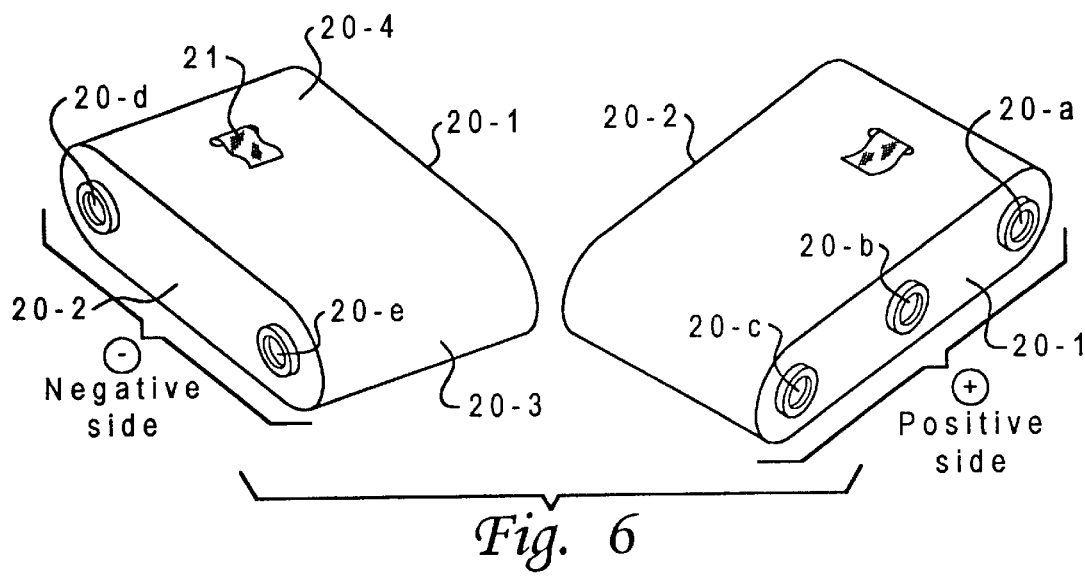
FIG. 6 is a right and left perspective view of a battery pack 20 according to the first embodiment of the present invention.

In FIG. 6 are perspective views, from the right and from the left, of the appearance of the battery pack 20 in this embodiment.

The battery pack 20 has an almost flat body, with front and rear semicircular faces 20-3 and 20-4, and has a footprint that is slightly smaller than the battery accepting unit 10. The box of the battery pack 20 is generally made of a strong and insulating material, such as polycarbonate. The battery pack 20 has a "multi-terminal structure", with three positive terminals, 20-a, 20-b and 20-c, being provided on the right side and two negative terminals 20-d and 20-e being provided on the left side. The terminals 20-a through 20-e correspond to the terminals 10-a through 10-e of the battery accepting unit 10 respectively. The circumferential edges of the terminals 20-a through 20-e are enclosed by ring-shaped projections. The ring-shaped projections are insulating components that are integrally formed with the box of the battery pack 20, and the outer diameter of the rings is smaller than the width of corresponding tongue-shaped recessed portions in the battery accepting unit 10. The ring-shaped projections are used to hold the battery pack 20 in the battery accepting unit 10, which will be described later, and can be expected to prevent a short-circuit due to contact with a conductive foreign substance. The semicircular sides 20-3 and 20-4 of the battery pack 20 are so formed that they have the same curvature as that of the side walls 10-3 and 10-4 of the battery accepting unit 10. As will be described later, the battery pack 20 is loaded into the battery accepting unit 10, a ribbon 21 being attached to the upper face of the battery pack 20 for easy removal.

Figure 7:
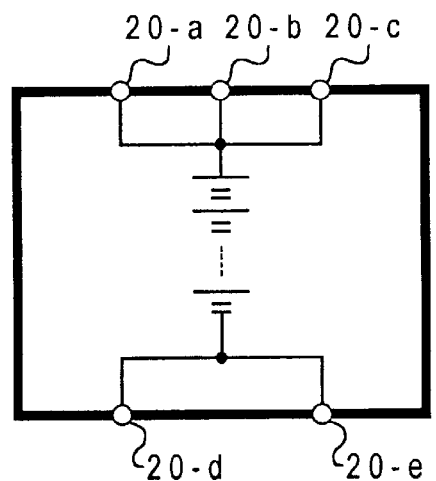
FIG. 7 is a schematic electric circuit diagram for the battery pack 20.

FIG. 7 is a schematic electric circuit diagram for the battery pack 20. The battery pack 20 is constituted by a series (or a parallel) connection of a plurality of battery cells, such as NiCd or NiMH cells. The number of battery cells is determined in accordance with the drive voltage and the capacity required by a PC, and is not related to the subject of the present invention.

The power line at the positive side branches to three lines that lead externally from the terminals 20-a, 20-b and 20-c. The power line at the negative side branches into two lines that lead externally from the terminals 20-d and 20-e.

The processing in the first embodiment and the method for loading/exchanging the battery pack 20 will now be described while referring to FIGS. 8 through 15.

Figure 8:
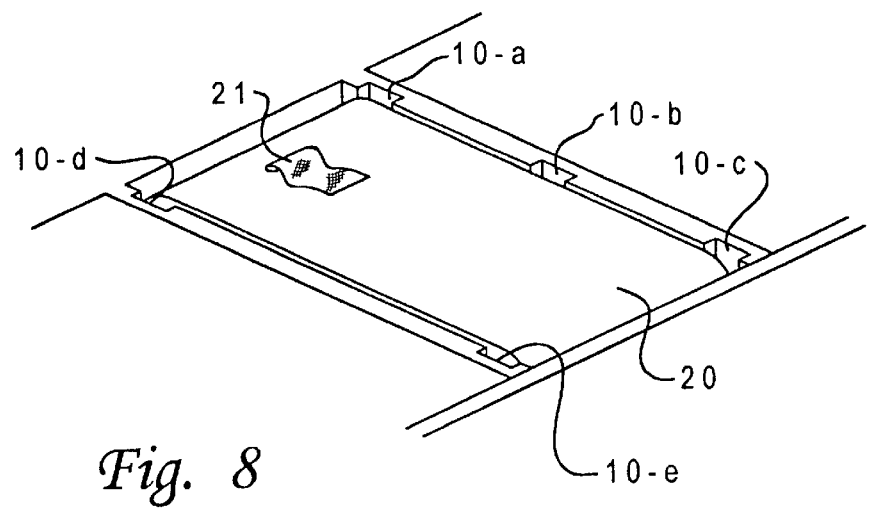
FIG. 8 is a diagram showing the state where the battery pack 20 is loaded in the battery accepting unit 10.

In FIG. 8 is shown the condition where the battery pack 20 is loaded in the battery accepting unit 10.

As is easily assumed from the above description, the battery pack 20 is so loaded that it is fully contained in the battery accepting unit 10 in the recessed portion under the keyboard 113 of the PC main body 110. The terminals 20-a through 20-e on the sides of the battery pack 20 are fitted to the corresponding terminals 10-a through 10-e of the battery accepting unit 10. The ring-shaped projections around the circumferential edges of the terminals 20-a through 20-e of the battery pack 20 have the same width as the tongue-shaped recessed portions formed at the corresponding terminals 10-a through 10-e of the battery accepting unit 10, as was previously described, and travel along the tongue-shaped recessed portions for attachment and removal. For attachment, the ring-shaped projections must move over the protruding portions of the contact elements 11 and counter the restoring force of the springs 14. Once the battery pack 20 is loaded, the contact elements 11 project outward into the rings and secure the battery pack 20.

Figure 9:
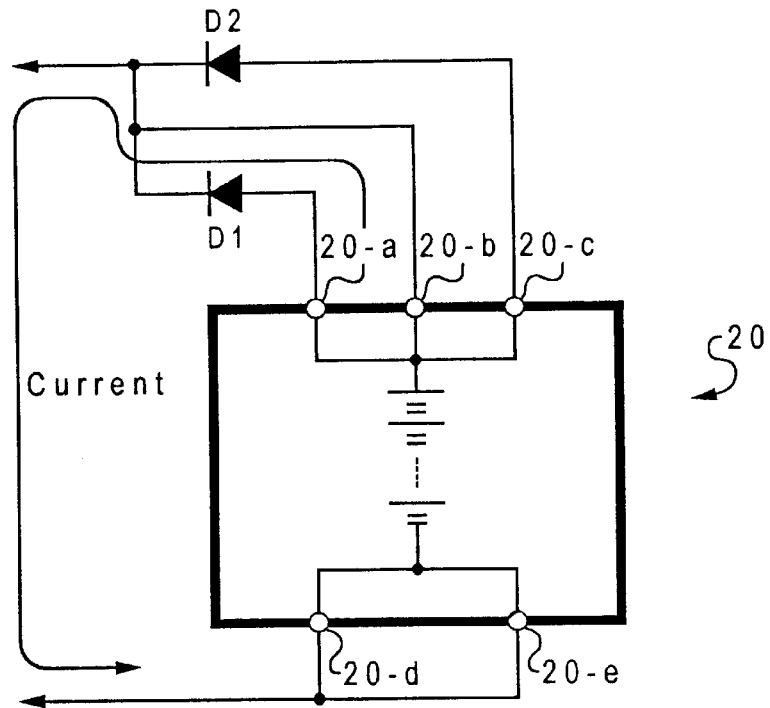
FIG. 9 is a schematic electric circuit diagram for the state where the battery pack 20 is loaded into the battery accepting unit 10.

FIG. 9 is an illustration of a schematic electric circuit diagram when the battery pack 20 is loaded into the battery accepting unit 10.

As is shown in FIG. 9, the positive pole of the battery pack 20 is electrically connected to the main body 110 of the PC 100 by all the terminals 20-a, 20-b and 20-c, and its negative pole is electrically connected to the terminals 20-d and 20-e. The diodes D1 and D2 are inserted for the positive terminals 20-a and 20-c in the forward direction for a discharge current of the battery, as was previously described. Although the three positive terminals are electrically connected, the internal resistance of the diodes D1 and D2 are present at the left and right terminals 20-a and 20-c, and thus a discharge current flows only from the middle terminal 20-b. Therefore, so long as the battery pack 20 is correctly loaded into the battery accepting unit 10 and normal battery operation is performed, a power loss due to a voltage drop in a forward direction of the diodes D1 and D2, or the heat generation that accompanies such a power loss, will not occur.

Figure 10:
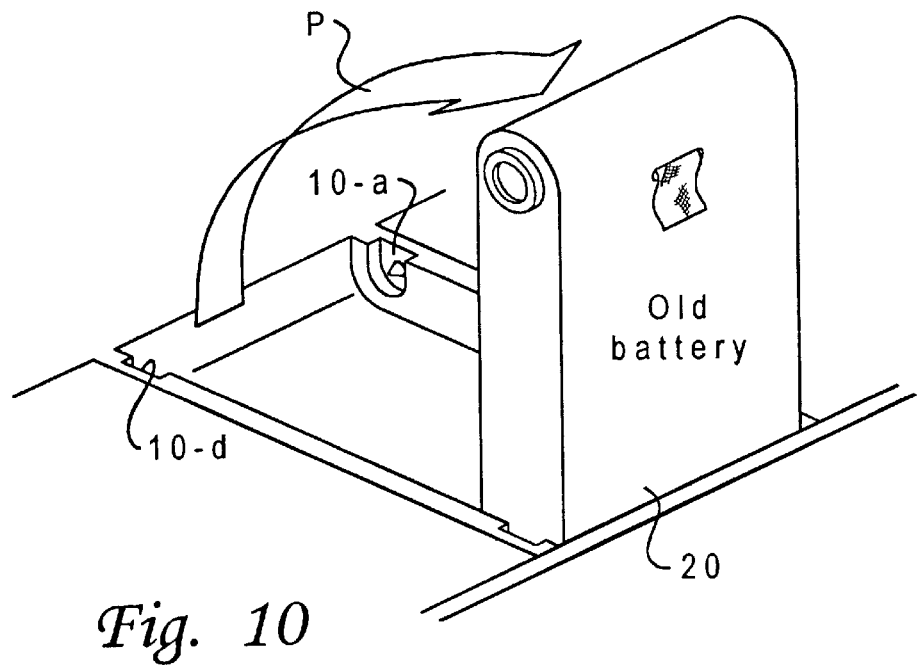
FIG. 10 is a diagram showing the condition where an old (or immediately before being over-discharged) battery pack 20 is being removed so that it can be replaced by a new (or fully charged) battery pack 20'.

FIG. 10 is a diagram showing the condition where an old (or immediately before being over-discharged) battery pack 20 is being removed so that it can be replaced by a new (or fully charged) battery pack 20'.

An operator pulls the ribbon 21 attached on the upper surface of the battery pack 20 in the direction indicated by an arrow P to remove the battery pack 20 from the battery accepting unit 10. The latching, which has existed between the terminals 20-a and 10-a, 20-b and 10-b, and 20-d and 10-d that are nearer to the ribbon 21, is released upon the exertion of a relatively strong torque in the direction of the tension force P. Since the torque is weaker at the terminals 20-c and 10-c, and 20-e and 10-e, which are away from the ribbon 21, the latching there is not released. As is shown in FIG. 10, therefore, the battery pack 20 is rotated along the line that runs through the terminals 20-c (10-c ) and 20-e (10-e ), and is lifted until it is standing upright. Since, as was previously described, the front and rear sides 20-3 and 20-4 of the battery pack 20 have semicircular shapes, and the front and rear walls 10-3 and 10-4 of the battery accepting unit 10 are bow shaped, the side faces 20-3 and 20-4 satisfactorily slide across the side walls 10-3 and 10-4 during the removal of the battery pack 20.

Figure 11:
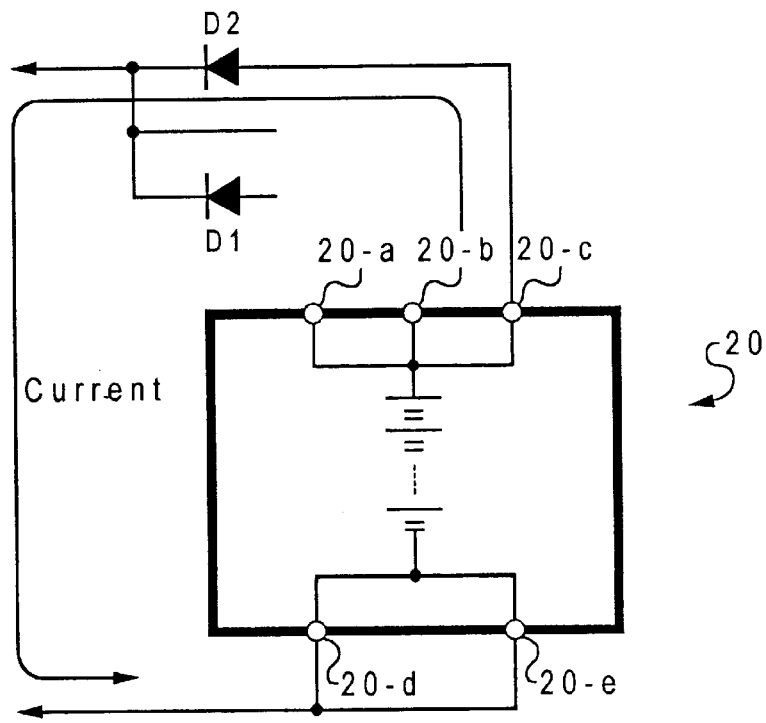
FIG. 11 is a schematic electric circuit diagram for the state where the battery pack 20 in FIG. 10 is being removed.

FIG. 11 is a schematic diagram of an electric circuit when the condition shown in FIG. 10, where the battery pack 20 is being removed, exists.

As is shown in FIG. 11, the battery pack 20 is electrically connected only at the output terminals 20-c and 20-e. The discharge current of the battery flows across the diode D2 in the forward direction.

Figure 12:
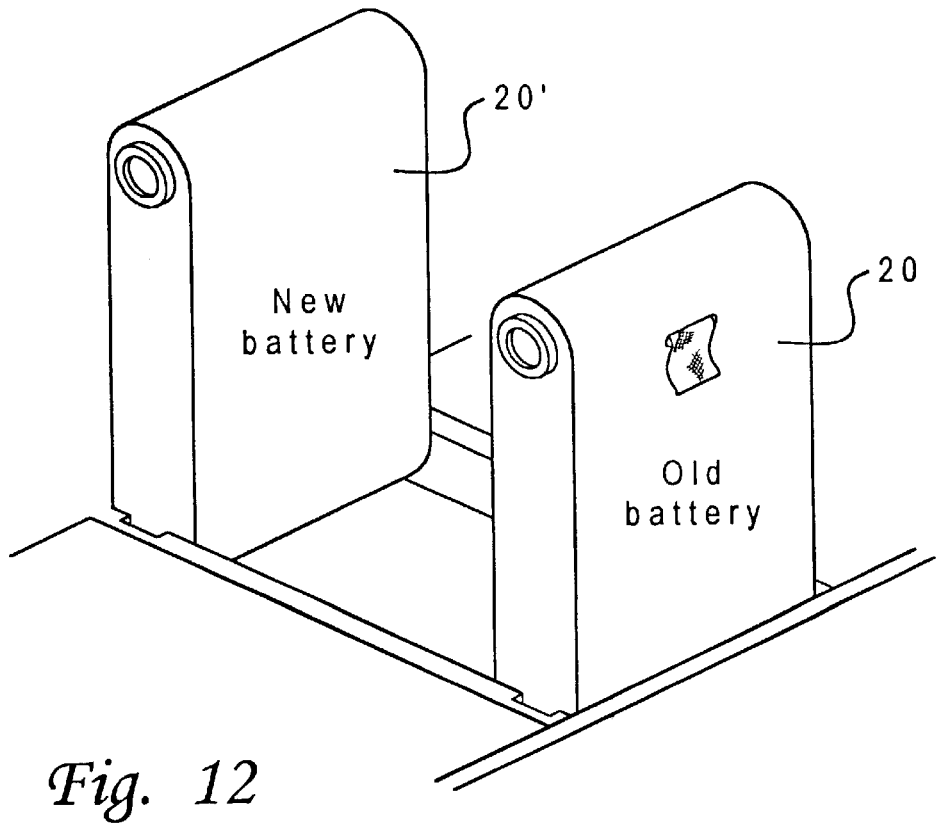
FIG. 12 is a diagram illustrating the state where an old battery pack 20 is being replaced by a new battery pack 20'.

In FIG. 12 is shown the condition that exists when an old battery pack 20 is being replaced by a new battery pack 20'.

When the old battery pack 20 is stood upright, the terminals 10-a and 10-d are released, as is shown in FIG. 10. Then, as is shown in FIG. 12, the new battery pack 20' can be inserted into the battery accepting unit 10 at the rear semicircular side face 10-3, i.e., the side at which the terminals 20-a and 20-d are located.

Figure 13:
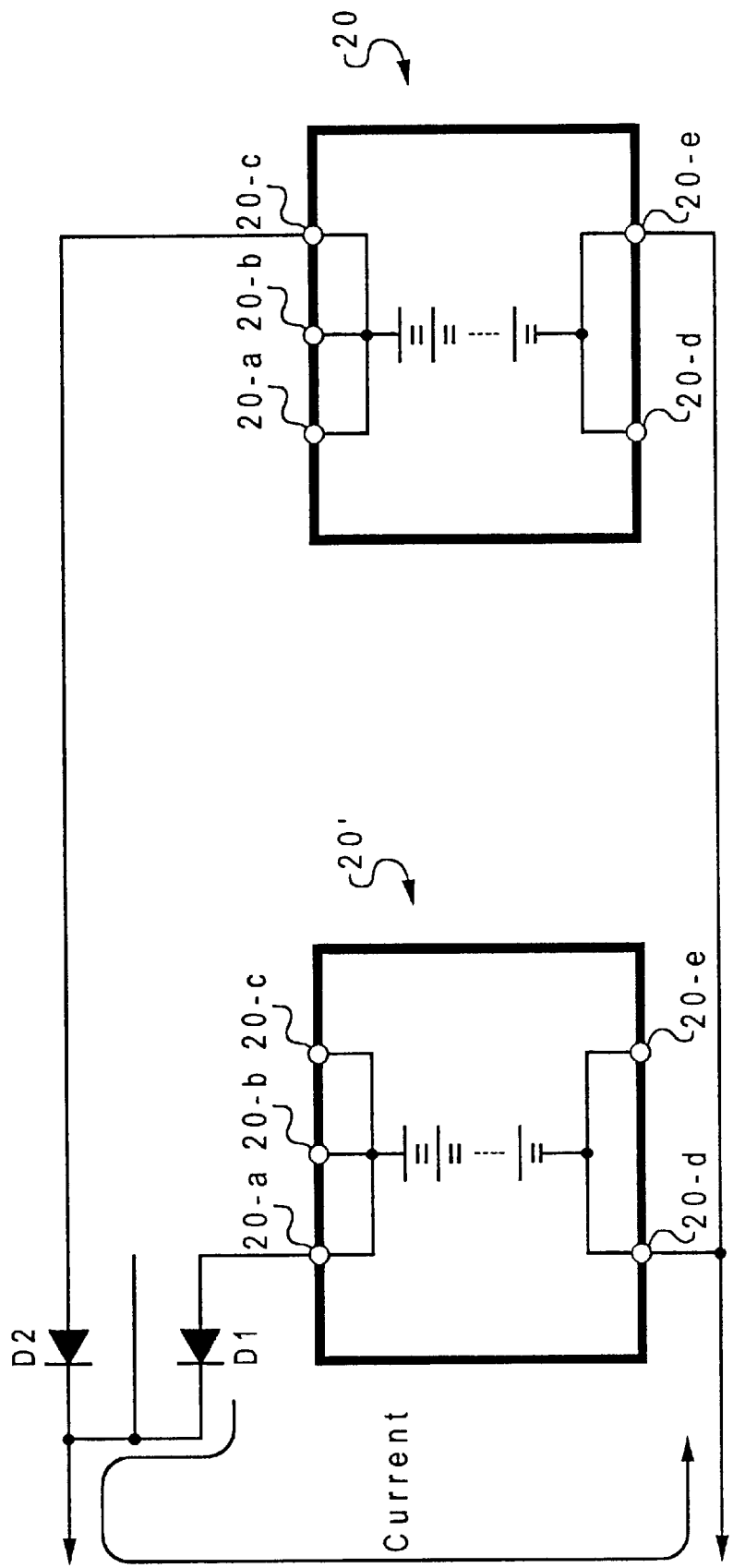
FIG. 13 is a schematic electric circuit diagram for the state shown in FIG. 12.

FIG. 13 is a schematic electric circuit diagram for the battery packs 20 and 20' when they are positioned as is shown in FIG. 12.

As is shown in FIG. 11, the old battery pack 20 is electrically connected at the terminals 20-c and 20-e, and the new battery pack 20' is electrically connected at the terminals 20-a and 20-d, which are disconnected on the old battery pack 20. Generally, when battery packs are being exchanged, the old battery pack 20 and the new battery pack 20' greatly differ in their output voltages and their remaining capacities. If the positive poles of the new and old batteries are short-circuited, a large current will flow from one battery to the other, and both batteries may be heavily damaged. In this embodiment, however, since between the positive poles of the battery pack 20 and 20' the two backflow prevention diodes D1 and D2 are so inserted that their cathodes face each other (as was previously described), such an electrode short-circuit will not occur.

Figure 14:
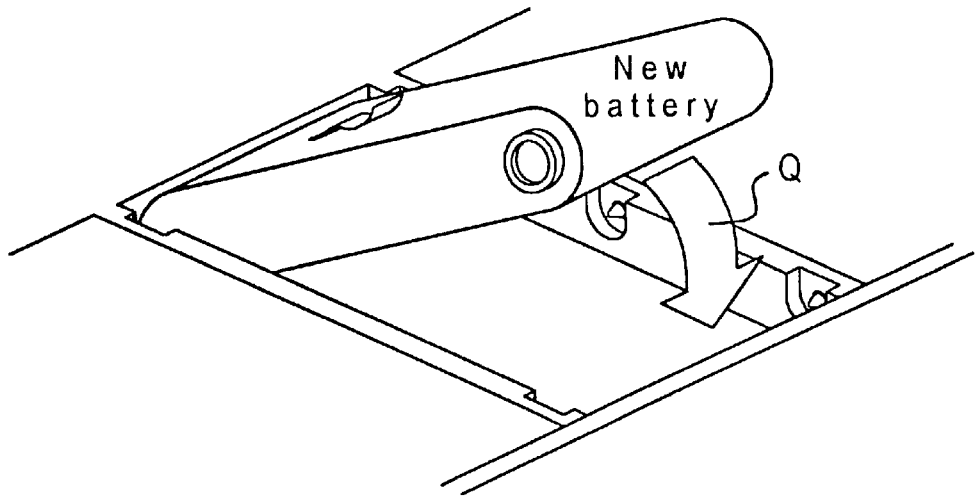
FIG. 14 is a diagram illustrating the state where a new battery pack 20' has been loaded into the battery accepting unit 10.

FIG. 14 is a diagram illustrating the condition where the new battery pack 20' is being loaded into the battery accepting unit 10.

When the old battery pack 20 (not shown) is pulled up, a predetermined force is required to release the latching action between the terminals 20-c and 10-c, and 20-e and 10-e. After the latching is released and as the battery pack 20 is removed, the circumferential portions of the ring-shaped projections are guided along the side faces of the tongue-shaped recessed portions.

Then, force in the direction indicated by an arrow Q is applied to the upper portion of the upright new battery pack 20'. The battery pack 20' is rotated around the line that runs through the terminals 20-a (10-a) and 20-d (10-d), and descends into the battery accepting unit 10. Since the semicircular side 20-4 of the battery pack 20' is moved across the bow-shaped side wall 10-4 of the battery accepting unit 10, a relatively small rotational force Q is required.

The ring-shaped projections at the terminals 20-c and 20-e are inserted into the tongue-shaped recessed portions at the terminals 10-c and 10-e, are moved over the contact elements by the rotational force Q and the weight of the battery pack 20' and are fitted into the recessed portions. The battery pack 20' is loaded as is shown in FIGS. 8 and 9, and the exchange process is thereafter terminated.

Figure 15:
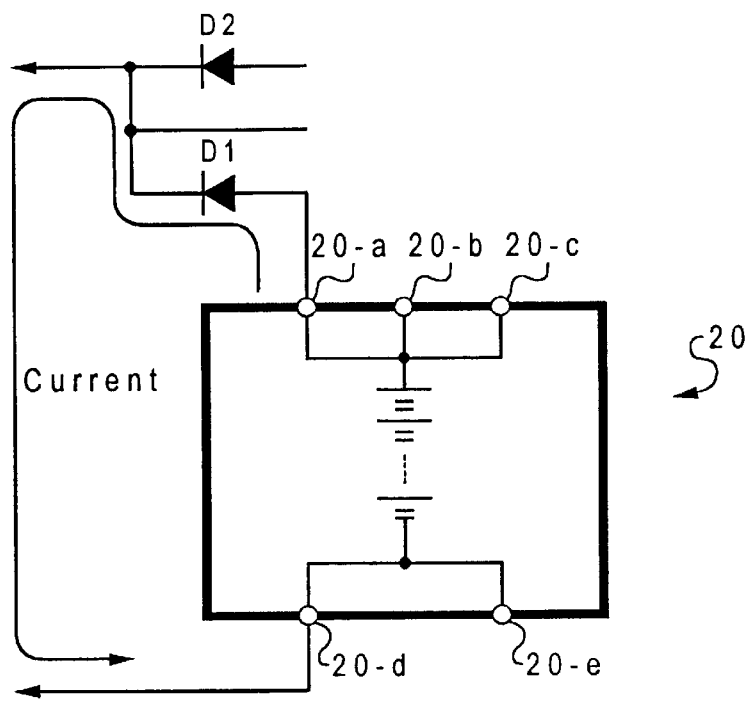
FIG. 15 is a schematic electric circuit diagram for the state shown in FIG. 14.

FIG. 15 is a schematic diagram of an electric circuit when the condition shown in FIG. 14 exists.

As is shown in FIG. 15, the battery pack 20', is electrically connected only at the output terminals 20-a and 20-d. Therefore, the discharge current of the battery flows forward across the backflow prevention diode D1.

It would be easily understood from the above explanation that the power supply to the PC 100 is not discontinued in the state shown in FIGS. 9, 11, 13 and 15. The PC 100 continues to operate without any particular change, and keeps providing complete protection for volatile data.

At the positions shown in FIGS. 11, 13 and 15, the battery discharge current flows across one or both of the diodes D1 and D2. However, this occurs only temporarily during a short period of time required when exchanging battery packs. When a battery pack is fully loaded, as is shown in FIG. 9, a discharge current flows only from the output terminal 20-b where no diode is present, and the problems that accompany a voltage drop in the forward direction, which is caused by the diodes D1 and D2, seldom occur.

Though not precisely shown in FIGS. 2 and 6, the outer diameters of the ring-shaped projections of the battery pack 20 and the widths of the tongue-shaped recessed portions of the battery accepting unit 10 are so formed that for each of their corresponding combinations there is a small difference in size. Therefore, incorrect loading of the battery pack 20, loading it other than in a predetermined direction, can be prevented.

Figure 19:
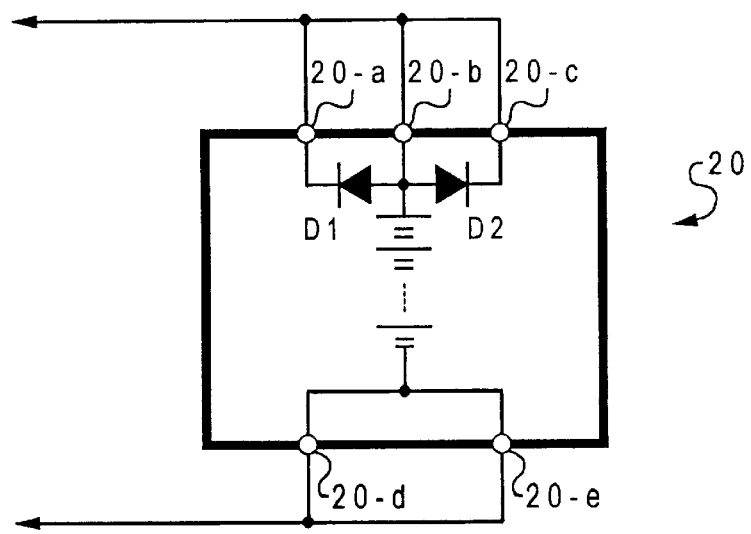
FIG. 19 is an electric circuit diagram showing a modification of the battery pack 20 and the battery accepting unit 10.

As is shown in FIGS. 3 and 7, in this embodiment the backflow prevention diodes D1 and D2 are provided for the battery accepting unit 10. As is shown in FIG. 19, however, the diodes may be loaded inside the battery pack 20. In this case, the amount of wiring required between the battery accepting unit 10 and the PC 100 can be reduced.

It should be understood from the subdivision A that, according to the first embodiment, the battery pack 20 can be exchanged without halting the power supply to the PC 100 and a sub-battery is not required as a backup during the battery pack exchange.

In the first embodiment, however, an operator can remove the battery pack 20 even when the power is supplied only by the battery pack 20 shown in FIG. 10. This is because, although the battery pack 20 is held by the latching action between the ring-shaped projections and the contact elements at the terminals 20-c and 20-e (previously described), the holding force exerted by the latching is relatively small. An impatient operator may not correctly follow the predetermined exchange procedures, and may completely remove the old battery pack 20 before it is backed up by the new battery pack 20', as is shown in FIG. 12, thus shutting down the power supply.

In a second embodiment, a mechanism (a "foolproof" mechanism) is provided for preventing the removal of an old battery pack 20 before a new battery pack 20' has been inserted.

Figure 16:
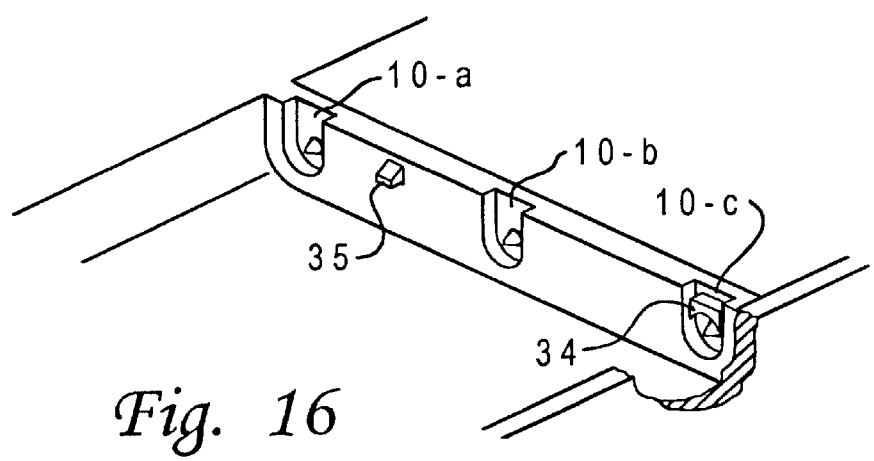
FIG. 16 is a perspective view of a battery accepting unit 10 according to a second embodiment of the present invention.
Figure 17:
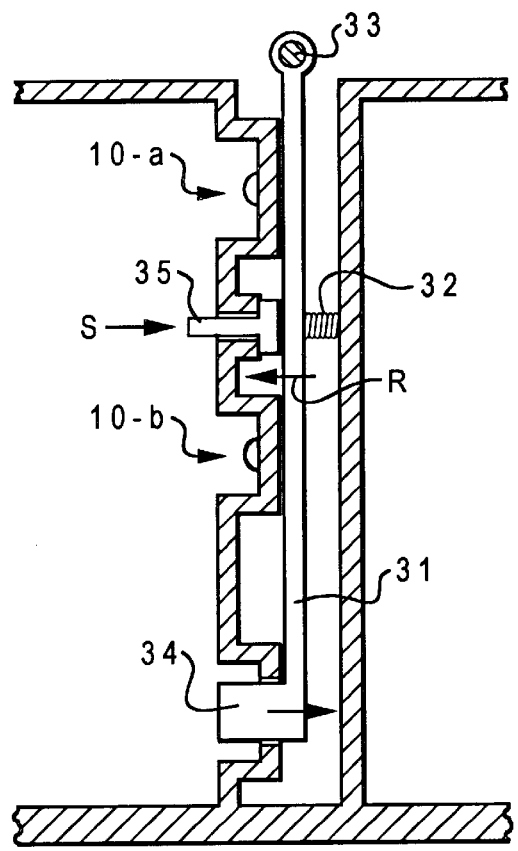
FIG. 17 is a horizontal cross sectional view of the battery accepting unit according to the second embodiment.

FIGS. 16 and 17 are a perspective view and a horizontal cross-sectional view of a battery accepting unit 10 according to the second embodiment. It should be understood that the portions not shown in these diagrams, and a battery pack 20, are the same as corresponding or identical portions in the first embodiment.

As is shown in FIG. 17, a chamber for holding a lever 31 is formed in the rear face of a right wall 10-1 of the battery accepting unit 10. The lever 31 is L-shaped and has a latch 34 at one end. At the opposite end, the lever 31 is rotatably supported at a support point 33, and is driven in a rotational direction, indicated by an arrow R, by the force exerted by a spring 32. This driving force causes the latch 34 to project outward through the opening formed at a terminal 10-c until its surface is even with that of the battery accepting unit 10 (see FIG. 16). The shape of the end of the latch 34 is so formed that it engages the outer surface of a ring-shaped projection of the battery pack 20. The latch 34 demonstrates a stronger latching action than that of contact elements formed on a relatively moderately curved face, which will be described later. A plunger 35, having a tapered tip, abuts upon the center of the lever 31. The rear face of the plunger 35 is pushed forward by the lever 31 so that the tapered tip projects outward through an opening formed in the vicinity of the terminal 10-a (see FIG. 16).

Although not shown in FIGS. 16 and 17, the same foolproof mechanism is internally provided for a left wall 10-2 of the battery accepting unit 10.

Figure 18:
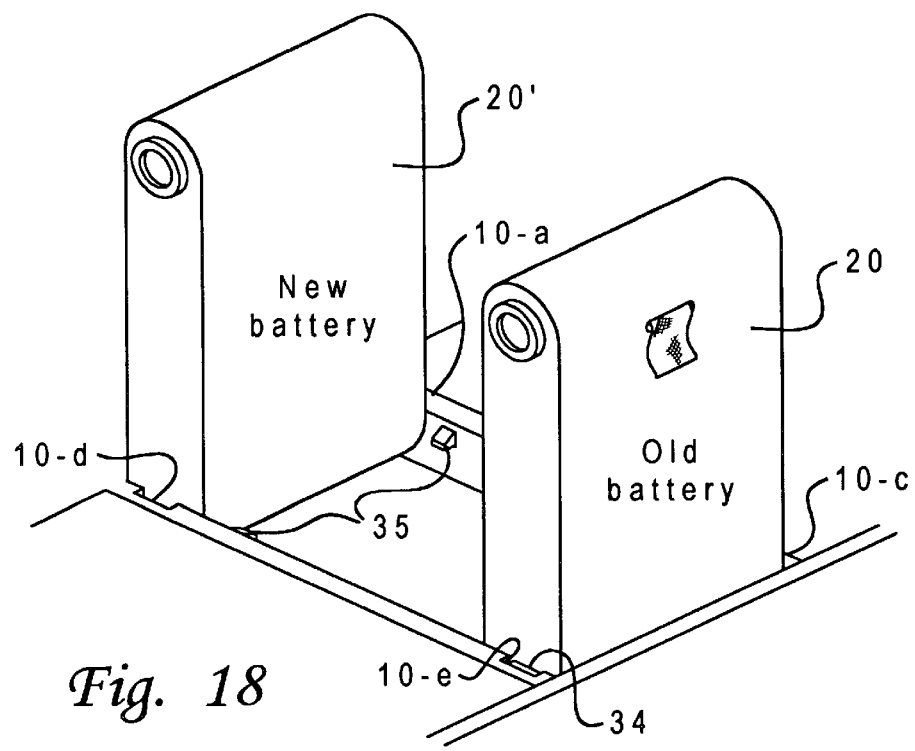
FIG. 18 is a diagram illustrating the condition where old and new battery packs 20 and 20' are being exchanged in the battery accepting unit 10 according to the second embodiment.
Figure 20:
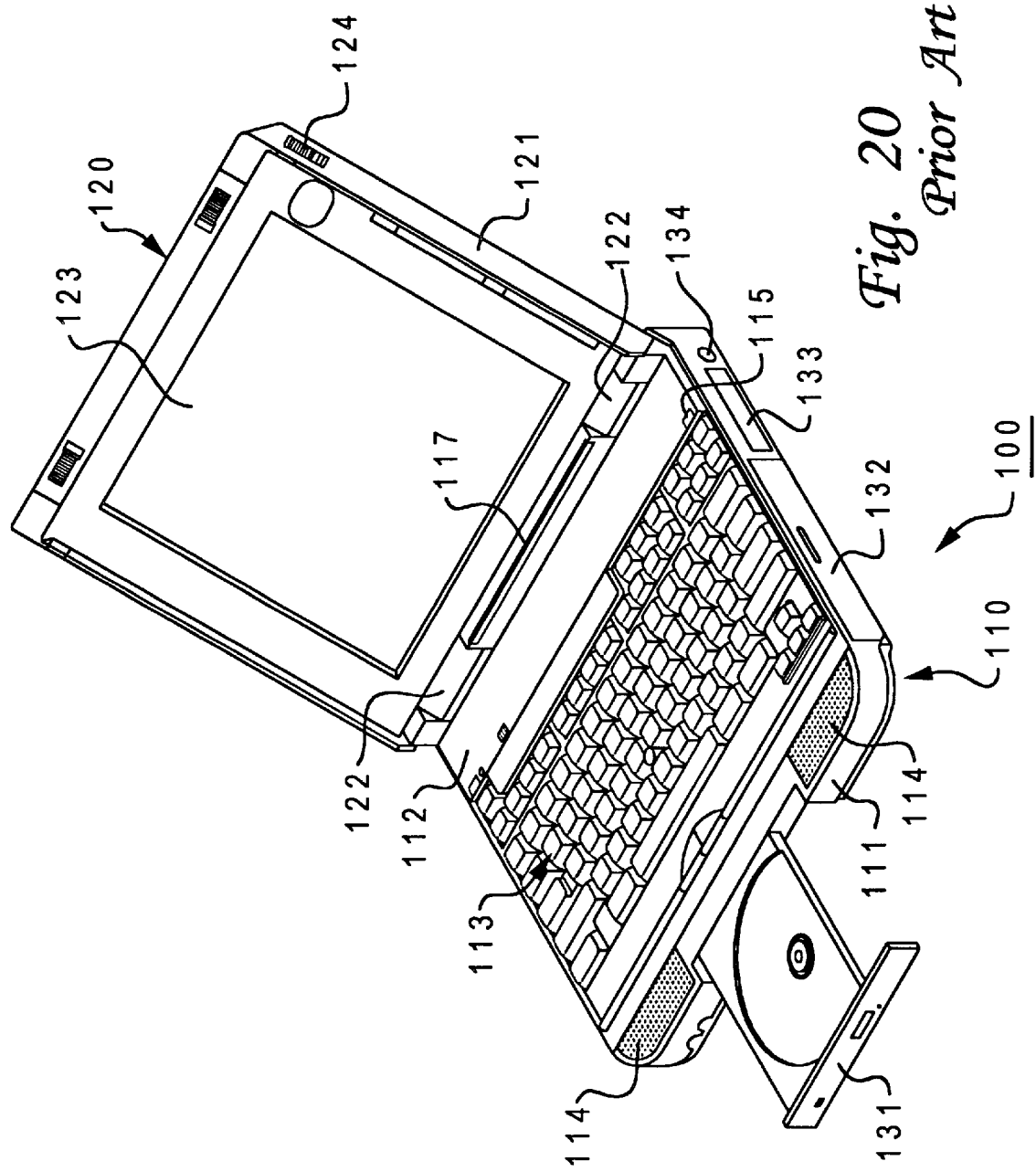
FIG. 20 is a diagram illustrating the appearance of a notebook computer (PC) 100.
Figure 21:
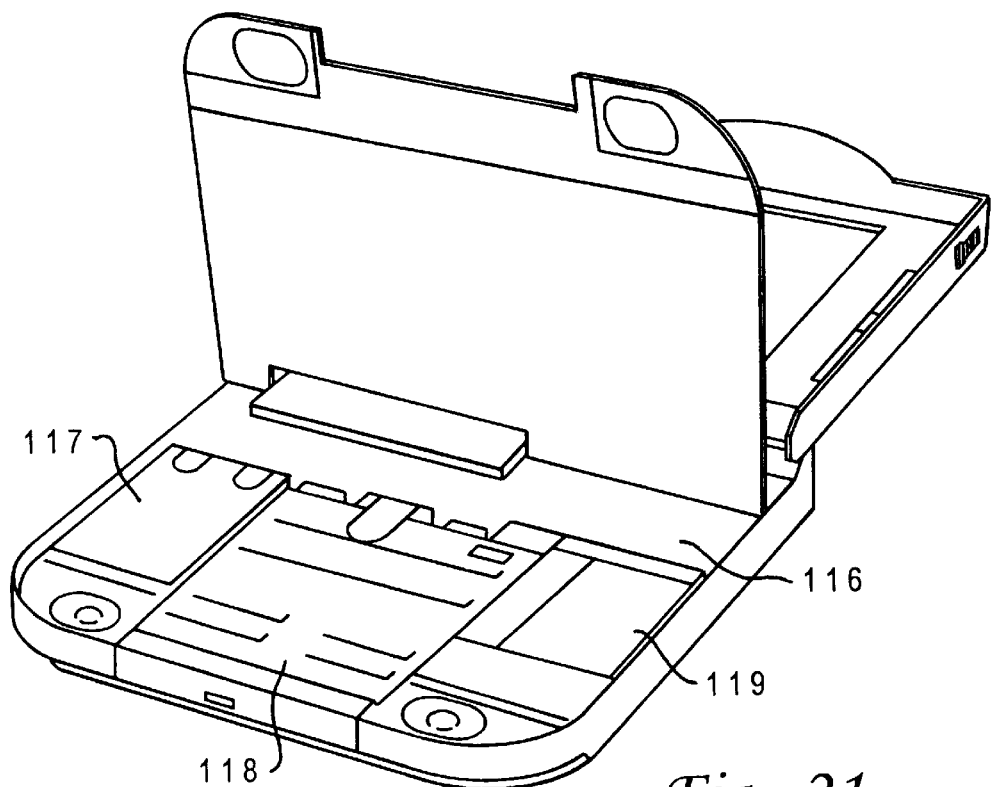
FIG. 21 is a diagram illustrating the condition where both a lid 120 and a keyboard 113 of the PC 100 have been opened to expose the internal structure of a main body.
Figure 22:
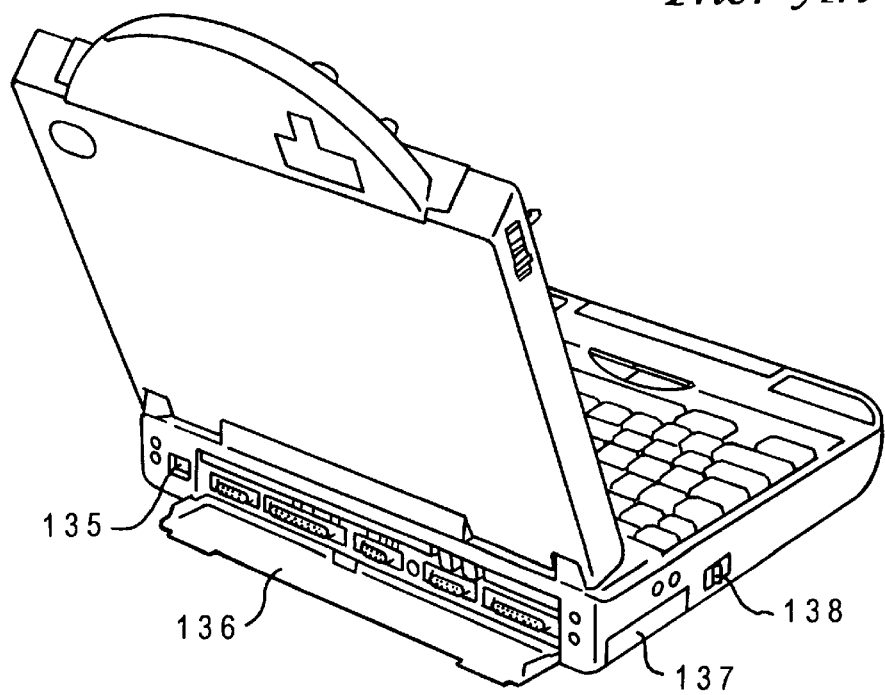
FIG. 22 is a perspective view of the PC 100 from the left rear.
Figure 23:
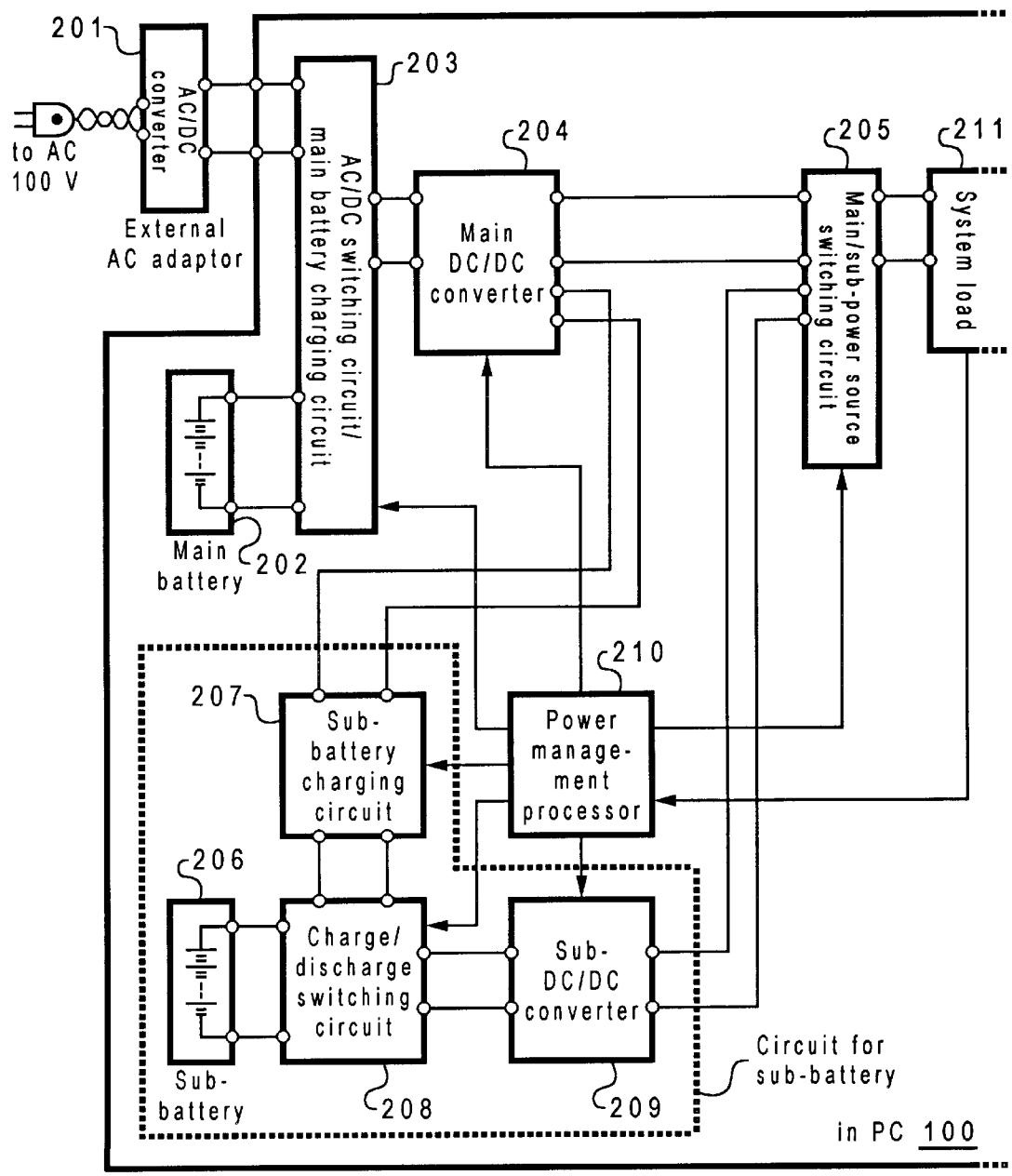
FIG. 23 is a diagram illustrating the conventional arrangement of a power supply system for a notebook computer 100 incorporating a sub-battery.

FIG. 18 is a diagram showing the state where the old and new battery packs 20 and 20' are exchanged in the battery accepting unit 10 according to the second embodiment.

When the new battery pack 20' is not yet loaded, or when it is being loading and is standing upright (see FIG. 18), the tip of the plunger 35 is not engaged, and only the rotational force exerted by the spring 32, in the direction indicated by the arrow R, is applied to the lever 31. As a result, the latch 34 engages the ring-shaped projection of the terminal 20-c of the old battery pack 20, and prevents its removal, even with the application of a relatively strong force.

As the new battery pack 20' is descending, the edges of the sides 20-1 and 20-2 contact the plungers 35. The tapered tips (previously described) of the plungers 35 are gradually pushed backward, as is indicated by an arrow S in FIG. 17, by the edges of the sides 20-1 and 20-2 as the battery pack 20' descends. Accordingly, the lever 31 is rotated, as is indicated by the arrow S, with the latch 34 being retracted inside. As a result, the ring-shaped projections of the terminals 20-*c* and 20-*e* are unlocked to permit the removal of the old battery pack 20.

Although, in this embodiment, the foolproof mechanism is provided in the battery accepting unit 10, it can be provided in the battery pack 20.

The present invention has been described in detail while referring to a specific embodiment. However, it should be obvious to one having ordinary skill in the art that various modifications or revisions of the embodiment are possible within the scope of the present invention. For example, the present invention can be applied to facsimile machines, various types of cordless machines, such as portable radio terminals, cordless telephones, electronic notebooks and video cameras, and battery operated electric/electronic apparatuses, such as word processors. That is, although the present invention has been disclosed by using an example, it should not be limited to that example. To fully understand the subject of the present invention, the claims should be referred to.

According to the present invention, provided is a superior battery accepting unit and a battery pack, for notebook computers, facsimile machines, various types of cordless machines, such as portable radio terminals, cordless telephones, electronic notebooks and video cameras, and battery operated electric/electronic apparatuses, such as word processors.

According to the battery accepting unit and the battery pack of the present invention, a battery pack can be exchanged without halting the power supply to an electric/electronic apparatus. Since an auxiliary power source, such as a sub-battery, is not required, a single power system, including a DC/DC converter and a charging circuit, can be provided. Therefore, the electric circuit in a system can be simplified, space can be saved inside a box, and manufacturing costs can be reduced.

We claim:

1. A battery powered device, comprising:
    a housing for accepting at least one battery having two ends;
    means for detachably rotatably coupling both ends of said at least one battery to said housing, on rotational axes parallel to said ends, such that either end of said at least one battery may be rotated out of said housing.

2. The battery powered device of claim 1, wherein said device has at least one power input and said coupling means further provides electrical coupling between said battery and said at least one power input.

3. The battery powered device of claim 1, wherein said coupling means comprises:
    a pair of terminals located on opposing surfaces of said housing, positioned at a first one of said ends; and
    a second pair of terminals located on opposing surfaces of said housing, positioned at a second one of said ends.

4. The battery powered device of claim 1, wherein said housing further includes a latch for securing a battery installed in said housing.

5. The battery powered device of claim 1, further comprising second coupling means for mechanically coupling a second battery to said housing.

6. The battery powered device of claim 5, wherein said second coupling means provides for detachably rotatably coupling said second battery.

7. The battery powered device of claim 5, wherein said device has at least one power input, said coupling means further provides electrical coupling between said battery and a first power input, and said second coupling means further provides electrical coupling between said second battery and a second power input.

8. The battery powered device of claim 5, further comprising backflow prevention means for preventing the flow of current from said first battery and said second battery.

9. The battery powered device of claim 5, wherein said housing further includes a latch for securing a battery installed in said housing.

10. The battery powered device of claim 5, wherein said latch is electrically operable.

11. The battery powered device of claim 10, further comprising detection means for detecting that said second battery has been electrically coupled to said housing, and said latch is disengaged responsive to an output of said detection means.

* * * * *